(12) United States Patent
Deckman et al.

(10) Patent No.: US 11,278,445 B2
(45) Date of Patent: Mar. 22, 2022

(54) IUD LOADING DEVICES AND METHODS FOR INSERTING AN IUD INTO AN INSERTION DEVICE

(71) Applicant: Medicines360, San Francisco, CA (US)

(72) Inventors: Rob Deckman, San Bruno, CA (US); Reilly Dillon, Golden Valley, MN (US); Mike Hoffman, Minneapolis, MN (US); Justin Westendorf, River Falls, WI (US); Dan Hovde, Montgomery, MN (US); Greg Vanhecke, Dassel, MN (US)

(73) Assignee: MEDICINES360, San Francisco, CA (US)

( * ) Notice: Subject to any disclaimer, the term of this patent is extended or adjusted under 35 U.S.C. 154(b) by 826 days.

(21) Appl. No.: 15/214,164

(22) Filed: Jul. 19, 2016

(65) Prior Publication Data

US 2017/0027739 A1 Feb. 2, 2017

Related U.S. Application Data

(60) Provisional application No. 62/198,961, filed on Jul. 30, 2015.

(51) Int. Cl.
*A61F 6/18* (2006.01)
*A61F 6/14* (2006.01)

(52) U.S. Cl.
CPC .............. *A61F 6/18* (2013.01); *A61F 6/144* (2013.01)

(58) Field of Classification Search
CPC ...... A61F 6/00; A61F 6/06; A61F 6/08; A61F 6/12; A61F 6/14; A61F 6/142; A61F 6/144; A61F 6/18; A61F 6/146; A61B 17/42; A61B 2017/1205; A61B 2017/12054
USPC ....... 128/830, 832, 834, 837, 838, 839, 840; 604/11, 15, 16, 18, 19, 27, 35–38, 43, 45, 604/264, 279, 358, 358.17, 500, 515
See application file for complete search history.

(56) References Cited

U.S. PATENT DOCUMENTS

| | | | |
|---|---|---|---|
| 3,783,861 A * | 1/1974 | Abramson | A61F 6/18 128/840 |
| 3,794,025 A | 2/1974 | Lerner | |
| 4,249,525 A | 2/1981 | Krzeminski | |
| 4,708,134 A | 11/1987 | Wildemeersch | |
| 4,920,727 A | 5/1990 | Ristimaki et al. | |
| 4,949,732 A | 8/1990 | Spoon et al. | |
| 5,084,004 A | 1/1992 | Ranoux | |
| 5,370,129 A * | 12/1994 | Diaz | A61F 6/18 128/839 |
| 5,400,804 A * | 3/1995 | Helle | A61J 3/00 128/898 |

(Continued)

FOREIGN PATENT DOCUMENTS

| | | |
|---|---|---|
| CN | 1081872 A | 2/1994 |
| CN | 1087507 A | 6/1994 |

(Continued)

*Primary Examiner* — Alireza Nia
*Assistant Examiner* — Rachel A Berezik
(74) *Attorney, Agent, or Firm* — Buchalter; Cecily Anne O'Regan

(57) ABSTRACT

Disclosed are devices and methods for loading an intrauterine device (IUD) with a thread or suture engaged therewith into an insertion device. The devices and methods are suitable for use with an automated knot tying system.

20 Claims, 8 Drawing Sheets

(56) References Cited

U.S. PATENT DOCUMENTS

| | | | | |
|---|---|---|---|---|
| 5,785,053 A * | 7/1998 | Macandrew | ............... | A61F 6/18 128/840 |
| 5,842,474 A * | 12/1998 | Blyskal | ................. | A61F 6/18 128/839 |
| 2010/0256662 A1 * | 10/2010 | Racenet | ................ | A61B 10/06 606/170 |
| 2013/0014762 A1 * | 1/2013 | Deckman | ................ | A61F 6/144 128/833 |
| 2013/0068234 A1 | 3/2013 | Pandit | | |
| 2014/0041667 A1 | 2/2014 | Cammack | | |
| 2016/0128729 A1 * | 5/2016 | Khurana | ............ | A61B 17/4241 606/119 |

FOREIGN PATENT DOCUMENTS

| | | |
|---|---|---|
| CN | 2183164 Y | 11/1994 |
| CN | 1168626 C | 9/2004 |
| CN | 1561186 A | 1/2005 |
| CN | 1830124 A | 9/2006 |
| CN | 104023681 A | 9/2014 |
| EP | 0147274 A1 | 7/1985 |
| WO | 20170019396 A1 | 2/2017 |

* cited by examiner

IUD LOADING DEVICES AND METHODS FOR INSERTING AN IUD INTO AN INSERTION DEVICE

CROSS-REFERENCE

This application claims the benefit of U.S. Provisional Application No. 62/198,961, filed Jul. 30, 2015, entitled *Loading Device for IUDs and Insertion Devices* which application is incorporated herein by reference.

BACKGROUND

An intrauterine device (IUD) is an object that, when placed in the uterus of a female, acts as a birth control device to prevent pregnancy. Two types of IUDs are commonly available, copper-containing devices and hormone-containing devices that release a progestogen. Hormonal containing devices are considered to be a different form of birth control and may be distinguished in the literature by the term intrauterine system (IUS).

IUDs are typically inserted into the uterus using an insertion device or instrument. See, for example, U.S. Pat. No. 3,783,861 to Abramson for Inserter for Intrauterine Devices issued Jan. 8, 1974; U.S. Pat. No. 3,794,025 to Lerner for Intrauterine Device Saddle Inserter issued Feb. 26, 1974; U.S. Pat. No. 4,920,727 to Ristimaki et al. for Cassette System and Apparatus for Manufacturing an Active Agent Liberating Capsule for Subcutnaeous Use issued May 1, 1990; U.S. Pat. No. 4,949,732 to Spoon et al. for Apparatus for Insertion and Fixation of an Intra Uterine Contraceptive Device to the Uterine Fundus issued Aug. 21, 1990; U.S. Pat. No. 5,084,004 to Ranoux for Process for Intra-Uterine Fertilization in Mammals and Device for Implementation Thereof issued Jan. 28, 1992; U.S. Pat. No. 5,370,129 to Diaz et al. for IUD Inserting Apparatus issued Dec. 6, 1994; U.S. Pat. No. 5,400,804 to Helle et al. for Method and Equipment for Installing a Medicine Capsule on a Support issued Mar. 28, 1995; U.S. Pat. No. 5,785,053 to Macandrew et al. for Inserter for the Positioning of an Intrauterine Device issued Jul. 28, 1998; and US 2013/0014762 A1 to Deckman et al. for Intrauterine Systems, IUD Insertion Devices, and Related Methods and Kits Therefor published Jan. 17, 2013.

During manufacturing of the system various challenges arise loading a threaded IUD into the distal end of the IUD insertion device such that the IUD is ready for deployment during use.

SUMMARY

Disclosed are intrauterine device (IUD) insertion device loaders and methods for loading an IUD with a flexible member, such as a thread or suture engaged therewith, into an IUD insertion device. The deployed IUD insertion device loaders and methods are suitable for use with an automated knot tying system.

An aspect of the disclosure is directed to an IUD loading device. Suitable IUD loading devices comprise: an elongated planar base having an upper surface and a lower surface; a linear slider engaging the upper surface of the planar base; a support plate secured to a portion of the linear slider; an IUD retainer; a clamp having a linear aperture therethrough and having a first clamp end and a second clamp end wherein the linear aperture at the first clamp end has a first diameter which tapers to a second aperture diameter central to the first clamp end and further wherein the linear aperture at the second clamp end has a first diameter which tapers to a second aperture diameter central to the second clamp end; and an inserter device retainer. Additionally, operation of the device can be controlled by pneumatic controls. Additionally, a vacuum applicator, such as a vacuum pump or venturi pump, can be provided in at least some configurations. The clamp may have a bivalve configuration that is openable about a hinge. Additionally, the insertion device retainer can include a hypotube. Additionally, the IUD retainer can comprise a channel for one or more flexible members of the IUD.

Another aspect of the disclosure is directed to an IUD loading device comprising: an elongated planar base having an upper surface and a lower surface; an IUD retainer; a clamp having a linear aperture therethrough and having a first clamp end and a second clamp end wherein the linear aperture at the first clamp end has a first diameter which tapers to a second aperture diameter central to the first clamp end and further wherein the linear aperture at the second clamp end has a first diameter which tapers to a second aperture diameter central to the second clamp end; an inserter retainer; and pneumatic controls configured to draw a flexible member of an IUD through the clamp and into an inserter. The clamp can be openable about a hinge. additionally, the insertion device retainer can be a hypotube. A channel can be provided for one or more flexible members of the IUD. Additionally a vacuum applicator, such as a vacuum pump or venturi pump, can be provided.

Still another aspect of the disclosure is directed to a method of inserting an IUD into an IUD insertion device. Suitable methods comprise: placing an IUD in an IUD retainer of an IUD loading device; positioning the IUD in the IUD retainer of the IUD loading device adjacent a first aperture in a clamp; placing an IUD inserter in an IUD inserter retainer of an IUD loading device; positioning the IUD inserter retainer of the IUD loading device adjacent a second aperture in the clamp; and applying a vacuum on the IUD inserter retainer and drawing one or more flexible members of the IUD into an aperture in the IUD insertion device. The methods can also include passing a hypotube through the IUD insertion device and/or feeding the flexible members of the IUD into the first aperture of the clamp.

Yet another aspect of the disclosure is directed to an IUD loading device means. Suitable IUD loading device means comprise: an elongated planar base having an upper surface and a lower surface; a linear slider means engaging the upper surface of the planar base; a support plate secured to a portion of the linear slider; an IUD retainer means; a clamp means having a linear aperture therethrough and having a first clamp end and a second clamp end wherein the linear aperture at the first clamp end has a first diameter which tapers to a second aperture diameter central to the first clamp end and further wherein the linear aperture at the second clamp end has a first diameter which tapers to a second aperture diameter central to the second clamp end; and an insertion device retainer means. Additionally, a pneumatic control or pneumatic control means can be provided. In at least some configurations a vacuum pump or vacuum pump means (e.g. venturi pump) is also provided. Additionally, the clamp means can be configurable to be openable about a hinge. The insertion device retainer means can be a hypotube. Additionally, the IUD retainer means can comprise a channel for one or more flexible members of the IUD.

Another aspect of the disclosure is directed to a method of inserting an IUD into an IUD insertion device comprising: placing an IUD in an IUD retainer means of an IUD loading device means; positioning the IUD in the IUD retainer means of the IUD loading device means adjacent a first aperture in a clamp; placing an IUD inserter in an inserter retainer means of an IUD loading device means; positioning the IUD inserter retainer means of the IUD loading device adjacent a second aperture in the clamp; and applying a vacuum on the IUD inserter retainer means and drawing one or more flexible members of the IUD into an aperture in the insertion device. Additionally, the method can include passing a hypotube through the IUD insertion device and/or feeding the flexible members of the IUD into the first aperture of the clamp.

Still another aspect of the disclosure is directed to an IUD loading device comprising: an elongated planar base means having an upper surface and a lower surface; an IUD retainer means; a clamp means having a linear aperture therethrough and having a first clamp end and a second clamp end wherein the linear aperture at the first clamp end has a first diameter which tapers to a second aperture diameter central to the first clamp end and further wherein the linear aperture at the second clamp end has a first diameter which tapers to a second aperture diameter central to the second clamp end; an inserter retainer means; and pneumatic control means configured to draw a flexible member of an IUD through the clamp means and into an inserter means. The clamp means can be openable about a hinge means. Additionally, the insertion device retainer means can be a hypotube. A channel can be provided for one or more flexible members of the IUD. Additionally a vacuum applicator means can be provided.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
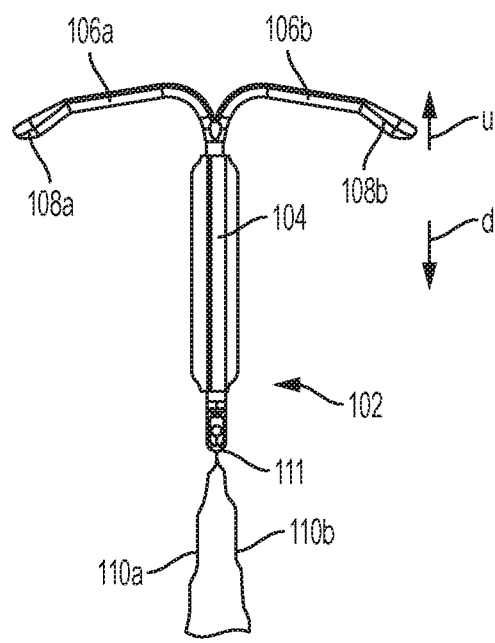
FIGS. 1A-D illustrate an IUD, an IUD positioned within the distal end of an IUD insertion device prior to deployment; an exemplar IUD insertion device, and a packaged IUD and IUD insertion device.

FIGS. 1A-D illustrates a T-frame intrauterine device (IUD), having an eyelet (aperture) at one end through which a flexible member, such as a thread or suture, is secured. A conventional T-shaped IUD 102, is illustrated in FIG. 1A. IUDs typically have a length of from about 31.5 mm to about 32.5 mm and a width of from about 31.5 mm to about 32.5 mm when the IUD is in the fully deployed position. As will be appreciated by those skilled in the art, the length does not include the knot or strings that may accompany the IUD. The T-shaped IUD comprises an elongated body 104 having a proximal end 10 and a distal end 20. The elongated body 104 can include a time-release drug such as a hormone. In some configurations, the time-release drug can be provided as a coating or covering. The elongated body can be formed from any suitable material, including, but not limited to plastic or metal alloy. At the distal end 20 of the IUD (i.e., the end positioned away from the physician's hand), IUD arms 106a, 106b are attached to or integrally formed with the elongated body 104. The IUD arms 106a, 106b are configurable to fold upward u or downward d to minimize the IUD cross-section such that the IUD can fit into an insertion device sheath or tube for insertion through the cervix and into the uterus during deployment. Additionally, either or both of the IUD arms 106a, 106b are configurable to include an enlarged or bulbous tip 108a, 108b, which can, for example, have a curved, spherical or semi-spherical shape. The bulbous tips 108a, 108b of the IUD arms 106a, 106b can be formed such that the IUD arms 106a, 106b, when folded upward and pushed together, form a smooth and rounded distal tip. At the proximal end 10 of the IUD 102, the IUD 102 can further include one or more flexible members 110a, 110b, such as strings, attached to the IUD 102. The flexible members 110a, 110b are connectable to the IUD 102 at a connection point 111 which can be an aperture or eyelet in the elongated body 104 at the proximal end 10, e.g., tied in a knot as illustrated.

For purposes of providing perspective to the various components of the loading device and the IUD and IUD insertion device, the relative terms of proximal and distal have been used where proximal refers to the end closest to the user and distal refers to the end further away from the user. Thus it is convenient to describe the loading device in a way which references the positioning of the proximal and distal ends of the IUD and the IUD insertion device. These references are provided for convenience of disclosure and are not meant to be limiting.

Figure 1B:
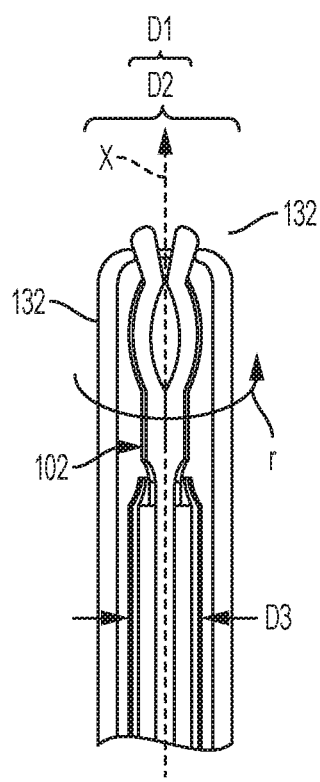
Figure 1C:
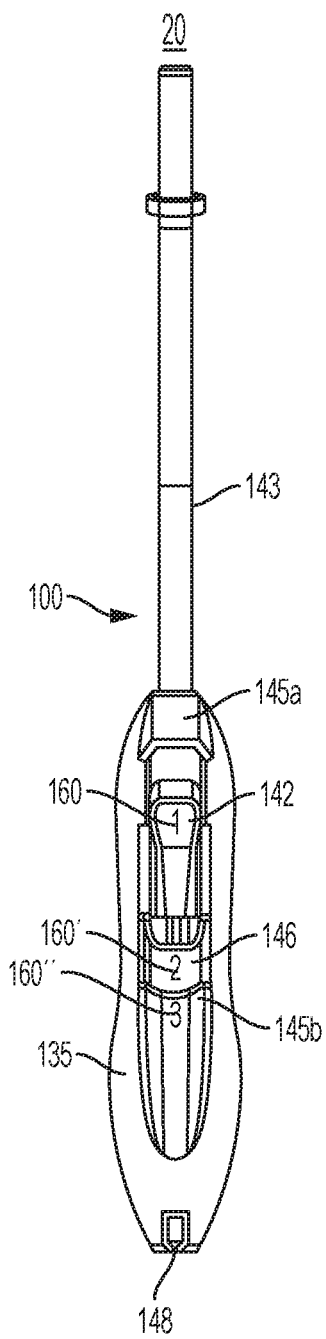

FIG. 1B is a cross-section of an insertion device (such as the insertion device shown in FIG. 1C). As can be seen in this illustration when the IUD 102 is positioned at the distal tip or the elongated sheath 132 of the IUD insertion device 100 prior to deployment, the distal 20 tip has an aperture 131 with a diameter d1 that is smaller than the diameter d3 of the IUD 102. The aperture of the IUD insertion device 100 has a diameter d1 that is smaller than the diameter d2 of the sheath of the IUD insertion device 100. The IUD 102 is rotatable r in-plane about longitudinal axis x, such that the IUD arms 106a, 106b or similar features of the IUD 102 will deploy in-line with respective openings of the patient's fallopian tubes.

An exemplar IUD insertion device 100 is illustrated in FIG. 1C. The IUD insertion device 100 is configurable to comprise a first cavity 145a and a second cavity 145b in the handle 135. During step 3 of the insertion procedure, the sheath slider 142 and string control slider 146 are in the full proximal 10 position along the longitudinal axis of the elongated guide, and at least partially surrounded by the second cavity 145b which is proximal to the first cavity 145a. Additional visual indication features 160, 160', 160" are shown. Visual indication features can be provided on the elongated sheath 143, the handle 135, or both. The numbers 1, 2, and 3 on the insertion device components provide a visual indication to the user the appropriate positions of the insertion device components during the multiple phases of the insertion procedure. Visual indicators, such as numbers, can be applied in any suitable fashion including, but not limited to, printing, etching, molding, stamping, and the like. Moreover, visual indicators can be positioned such that they are visible only during certain aspects of the procedure, and not visible during other aspects of the procedure.

Figure 1D:
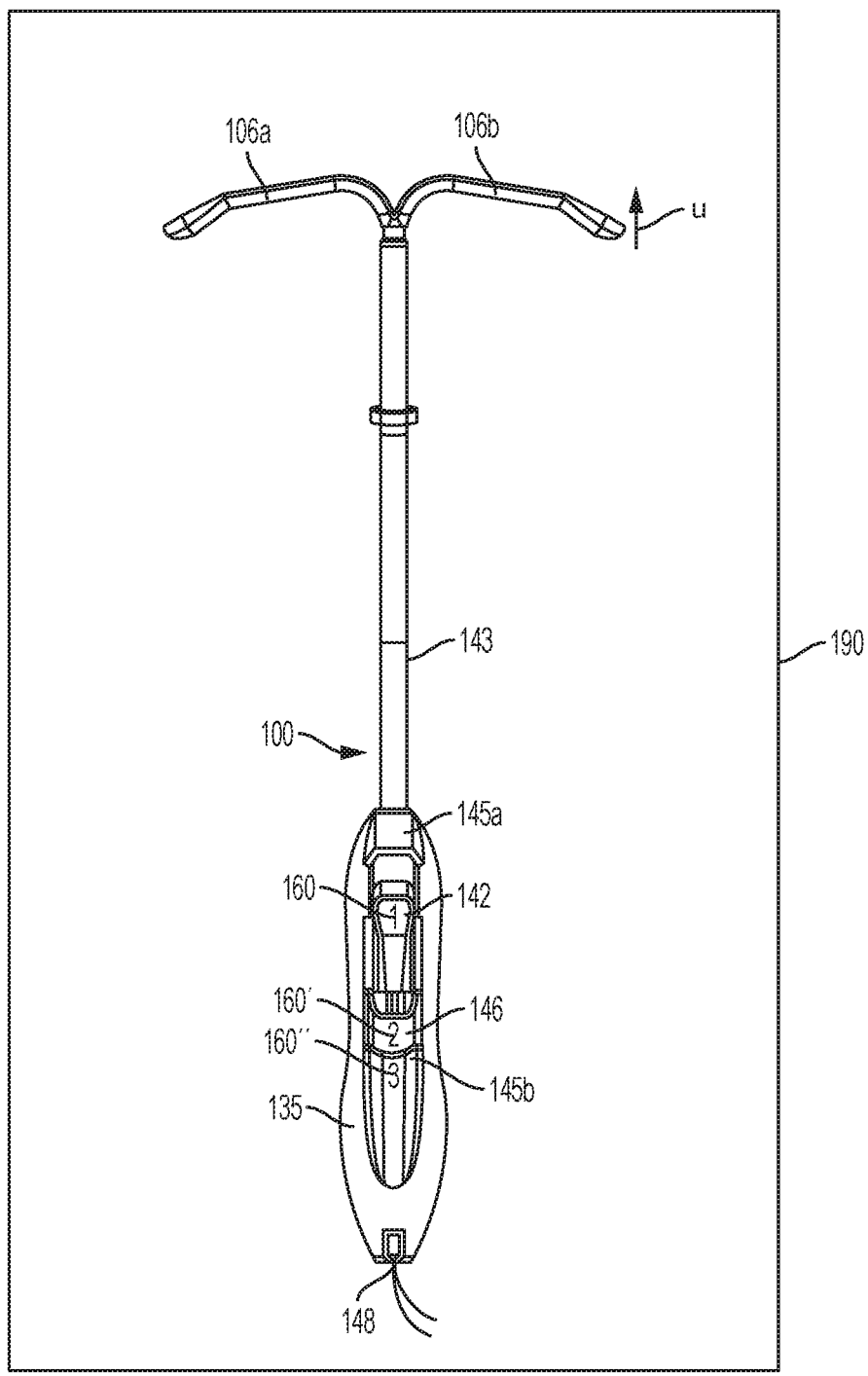

FIG. 1D illustrates an IUD partially positioned within the distal end of an IUD deployment device within packaging 190. The IUD arms 106a, 106b extend beyond the distal end of the IUD deployment device 100.

Figure 2A:
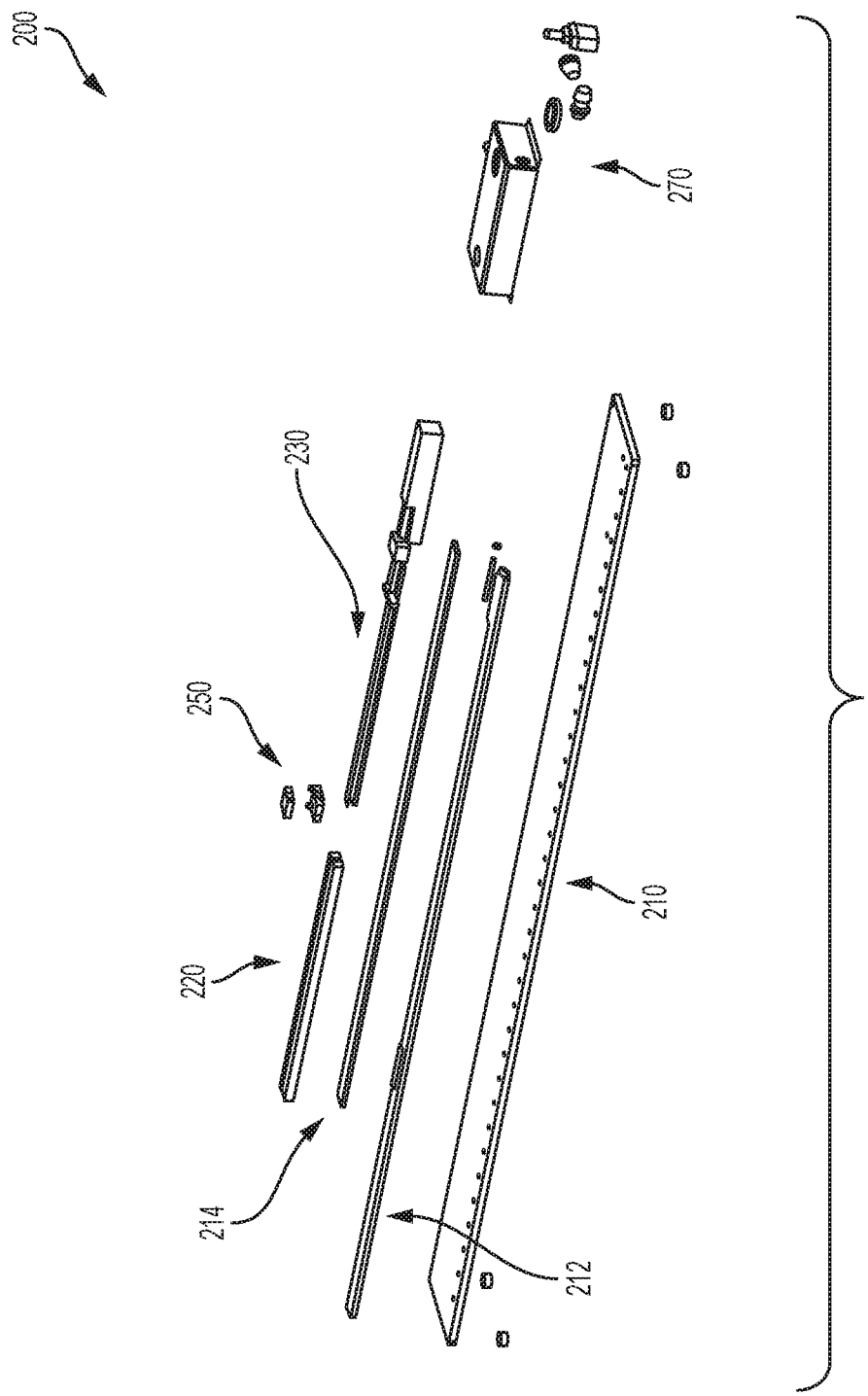
FIGS. 2A-C is an exploded view of a IUD insertion device loader for use associating an IUD with an IUD insertion device; a close-up of the hinged member; and a perspective view of the IUD insertion device loader in an assembled form.

FIG. 2A is an exploded view of an IUD insertion device loader 200. The IUD insertion device loader 200 has an elongated planar base 210 which supports a linear slider 212. A support plate 214 can also be provided which engages the linear slider 212. An insertion device retainer 230 is provided and is configurable to engage the insertion device (such as the IUD insertion device 100 shown in FIG. 1C) during the loading process. An IUD retainer 220 is positioned in-line with the insertion device retainer 230 and positioned above the support plate 214. A clamp 250 is positioned between the IUD retainer 220 and the insertion device retainer 230. Pneumatic controls 270 can be provided at one end of the assembly to apply a vacuum, for example on an end of the assembly having the insertion device retainer 230. The vacuum can be applied by any suitable vacuum applicator, such as a vacuum pump or venturi pump. The pneumatic controls can include pneumatically controlled valves that control the flow of pressurized air. Suitable valves include, for example, needle valves. The support plate 214 can engage the linear slider 212 and elongated planar base 210 by any suitable mechanism including, for example, the use of screws, bolts, washers, nuts, adhesive materials, or any other suitable material or device.

Figure 2B:
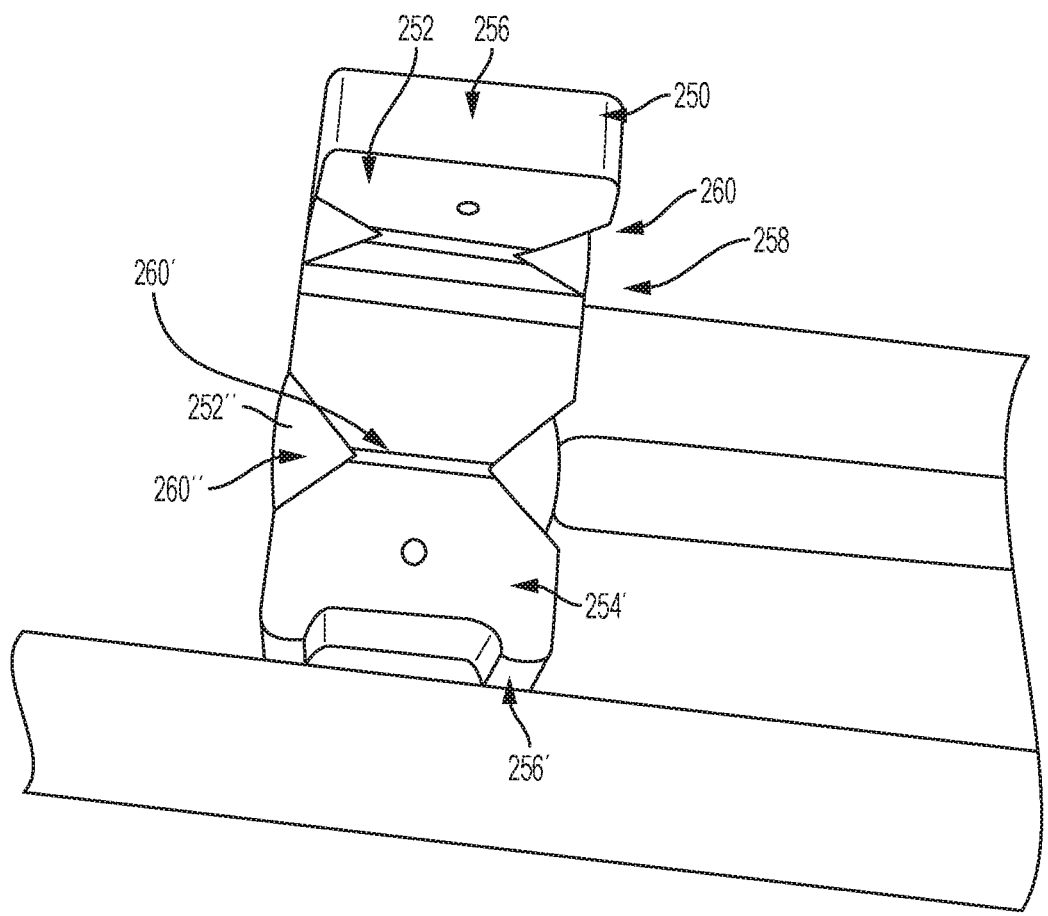

FIG. 2B is a close-up of the clamp 250 in an open configuration which, when closed, has an aperture therethrough forming a channel 252 formed in one or both the surfaces of the interior surfaces 254, 254' of the clamp 250. In one configuration, the clamp 250 is a bivalve having two similar parts hinged together. The two parts or plates 256, 256' of the clamp 250 open and close about a hinge 258. When the clamp 250 is closed an aperture extends linearly from a first end to a second end. The aperture has a first recess 260 on the first end, followed by a central tubular portion 260' forming an interior portion of the aperture, and then a second recess 260" on the second end. As illustrated the first and second recesses are shaped to define a conical aperture where the widest portion of the aperture is adjacent the exterior surface of the clamp 250, and the narrowest portion is adjacent the central tubular portion 260'. As will be appreciated by those skilled in the art, other shapes could be used without departing from the scope of the disclosure. During use, the clamp 250 can be secured in a closed position using any suitable mechanism, including, but not limited to the use of magnetic material, suitable clasps or pins.

Figure 2C:
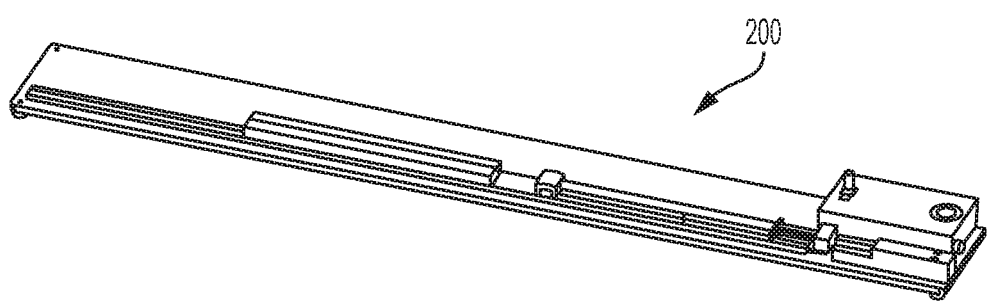
Figure 3A:
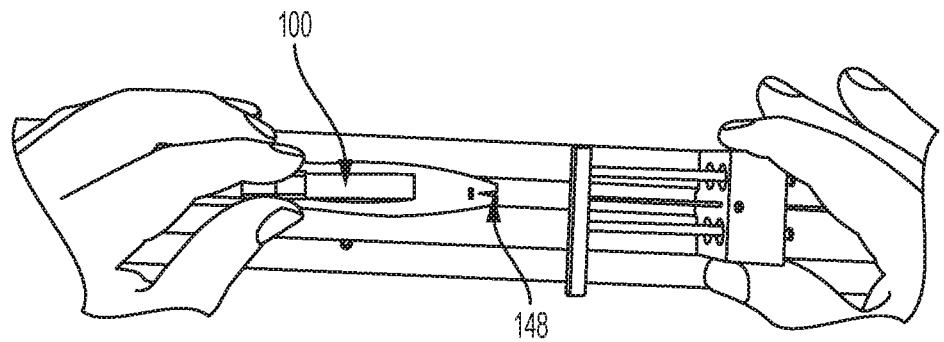
FIGS. 3A-G illustrate the steps of using the IUD insertion device loader.
Figure 3B:
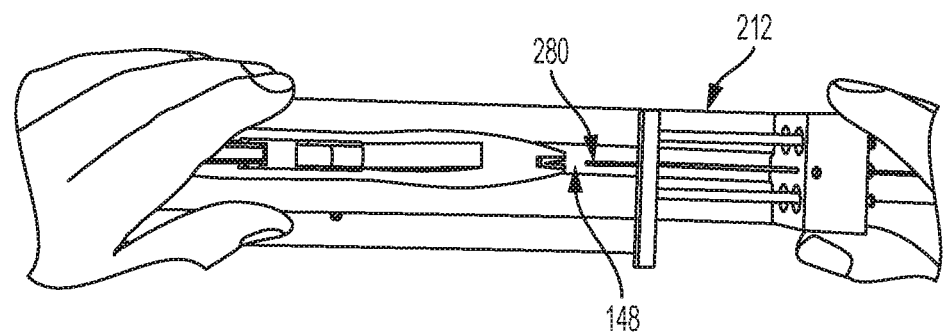
Figure 3C:
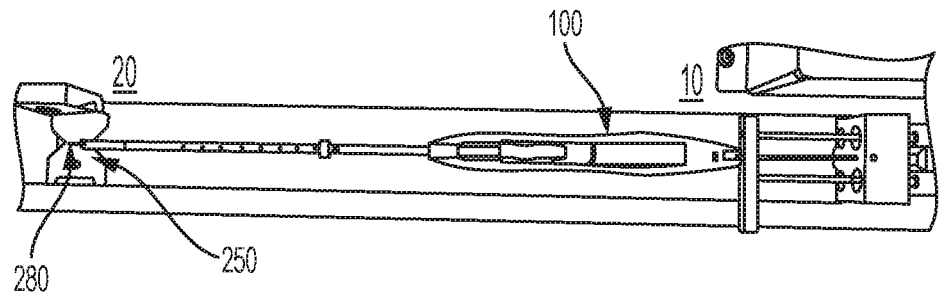
Figure 3D:
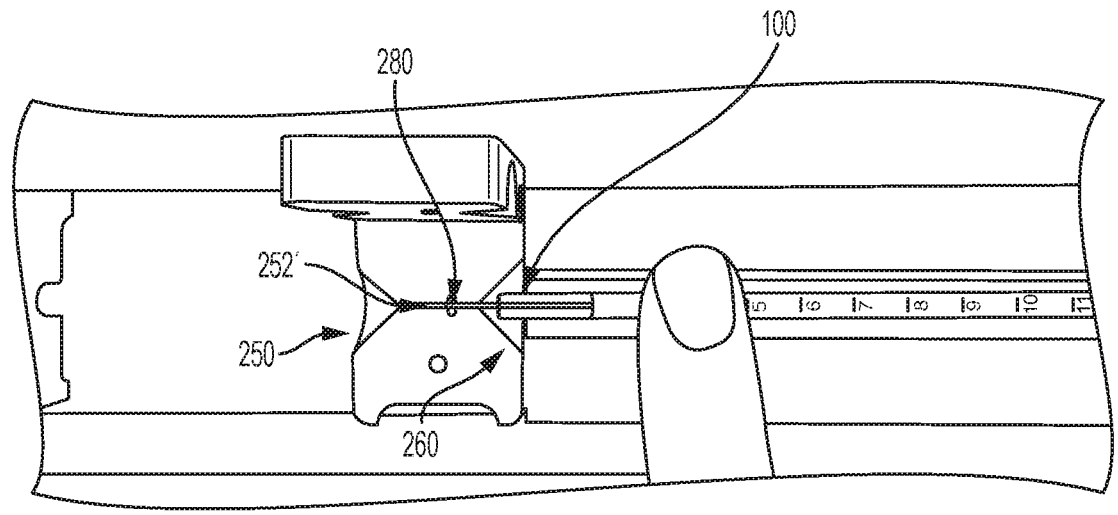
Figure 3E:
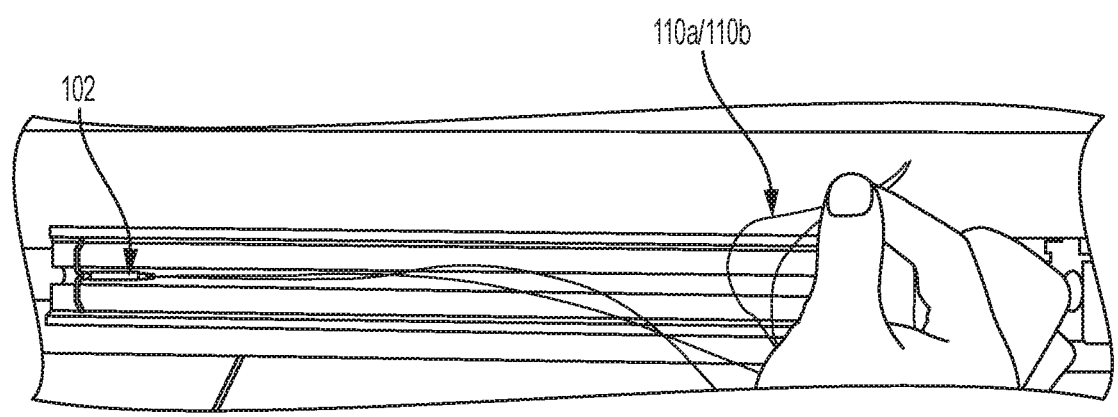
Figure 3F:
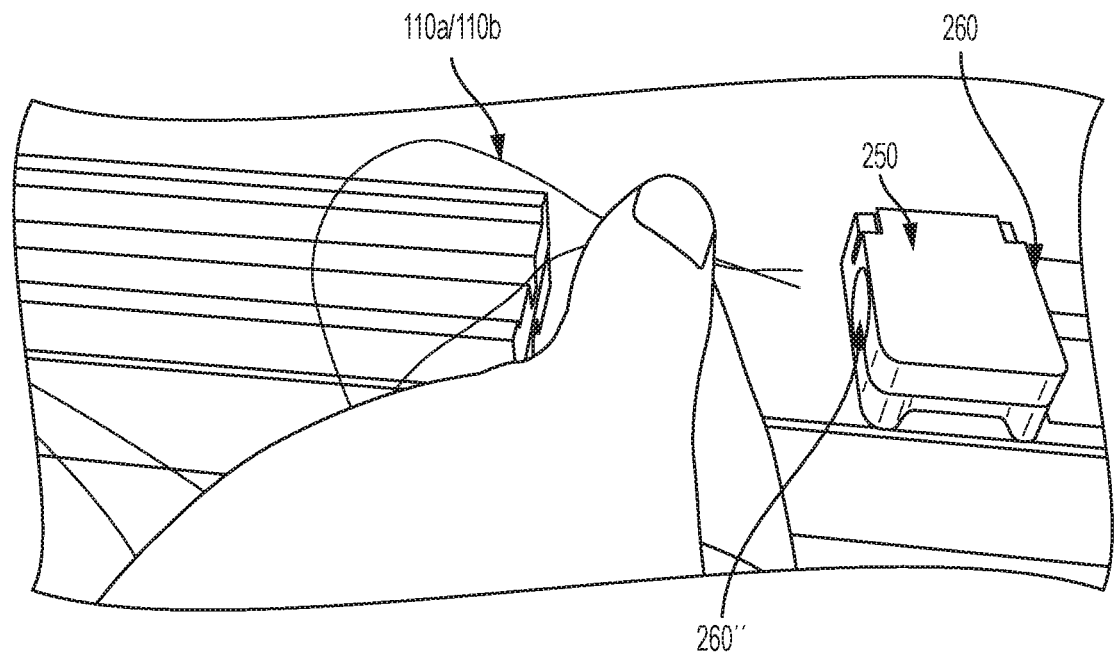
Figure 3G:
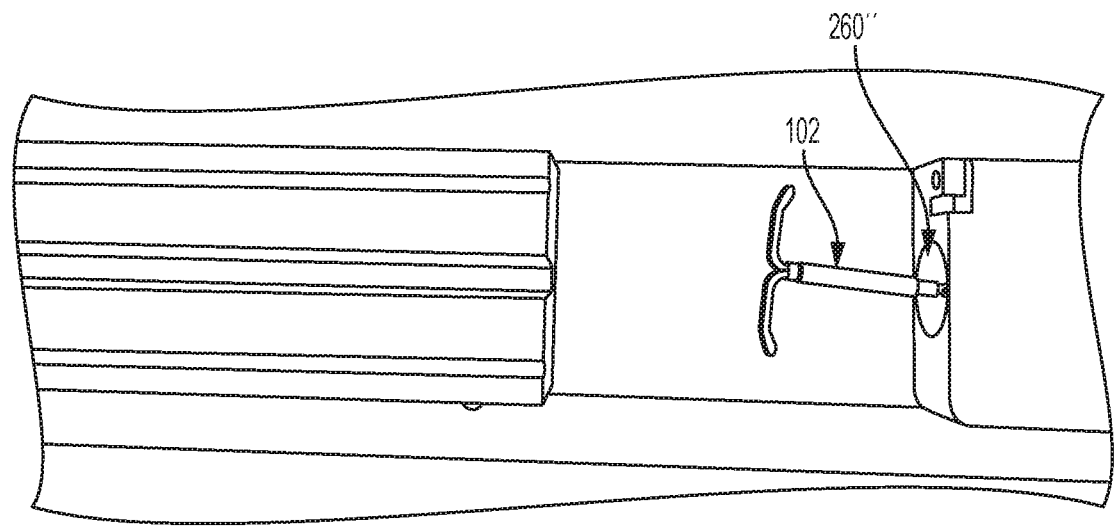

FIG. 2C illustrates the IUD insertion device loader 200 shown in FIG. 2A in an assembled configuration.

FIGS. 3A-G illustrate the steps of using the IUD insertion device loader 200 shown in FIG. 2. The IUD insertion device 100 is placed on the insertion device retainer 230. A hypotube 280 of the IUD insertion device loader 200 is inserted into a proximal aperture 148 of IUD insertion device 100. A suitable hypotube 280 is a small radiused tube which can, for example, be made from stainless steel. The hypotube 280, passes through a central aperture of the IUD insertion device 100 from the proximal end 10 until it exits a distal end 20 of the IUD insertion device 100. The end of the hypotube 280 extending out of the distal end of the IUD insertion device 100 is placed within the central channel 260' formed in the clamp 250 while the clamp 250 is in an open position (shown in FIG. 2B). The distal end 20 of the IUD insertion device 100 is positioned within the first recess 260 which is a conical aperture formed at the insertion device receiving end of the clamp 250. The positioning of the IUD insertion device 100 is such that the distal end 20 of the IUD insertion device 100 is not pinched by the clamp 250 when the clamp 250 is in a closed positon (shown in FIG. 3F), or otherwise engaged by the clamp 250 to cause deformation of the distal end 20 of the IUD insertion device 100. The IUD 102 is placed within the IUD retainer 220 so that the flexible members 110a, 110b, or strings, are positioned near the IUD receiving conical opening 252" of the clamp 250. The end of the strings or flexible members 110a, 110b are positioned near enough the IUD receiving conical recess 252" of the clamp 250 so that when the vacuum is applied by the vacuum applicator to the hypotube passing through the IUD insertion device 100 into the clamp 250, the strings or flexible members 110a, 110b are placed a centimeter or two inside the inner channel 252' of the clamp/hypotube and then the vacuum draws the flexible members 110a, 110b through the remainder of the IUD insertion device.

Thereafter, the clamp 250 is opened, and the IUD 102 is drawn into a final position within the IUD insertion device 100 so that the IUD 102 and IUD insertion device 100 are ready to be packaged and shipped as shown in FIG. 1D.

Once the IUD is positioned within the IUD inserter device, the device can be packaged, sterilized and shipped.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A loading device for loading an IUD into a distal end of an IUD insertion device during a manufacturing process wherein the IUD insertion device comprises an elongated sheath, and a plunger disposable within a lumen of the elongated sheath, a handle, and an IUD insertion device slider positioned on the handle of the IUD insertion device in communication with the plunger, the IUD comprises a t-shaped body with an elongated body and a flexible member secured to an end of the elongated body, and further wherein the loading device comprises:

an elongated planar base having a first planar base end, a second planar base end, an upper surface and a lower surface configured to engage the IUD insertion device on the upper surface of the elongated planar base of the loading device;

a linear loading device slider positioned on the upper surface of the elongated planar base;

a support plate secured to a portion of the linear loading device slider;

a hinged loading device clamp positioned on the upper surface of the elongated planar base of the loading device towards the first planar base end having an open configuration and a closed configuration, wherein the hinged loading device clamp defines a linear aperture therethrough in the closed configuration, further wherein the hinged loading device clamp has a first clamp end positionable to engage the elongated sheath of the IUD insertion device at the distal end of the IUD insertion device in the closed configuration and a second clamp end configured to receive the elongated body of the IUD, and further wherein the linear aperture of the hinged loading device clamp has a first clamp end aperture diameter which tapers to a central aperture diameter and a second clamp end aperture diameter which tapers to the central aperture diameter;

an IUD insertion device retainer positioned on the upper surface of the elongated planar base of the loading device towards the second planar base end wherein the IUD insertion device retainer is configured to be inserted within a portion of the handle of the IUD insertion device to secure the IUD insertion device to the loading device; and an IUD retainer positioned adjacent the second clamp end wherein the IUD retainer holds the IUD prior to loading the IUD into the distal end of the IUD insertion device during the manufacturing process.

2. The loading device of claim 1 further comprising a pneumatic control.

3. The loading device of claim 1 further comprising a vacuum applicator.

4. The loading device of claim 1 wherein the hinged loading device clamp is openable about a hinge.

5. The loading device of claim 1 wherein the IUD insertion device retainer is a hypotube sized to fit within a distal aperture of the IUD insertion device.

6. The loading device of claim 1 wherein the IUD retainer comprises a channel for one or more flexible members of the IUD.

7. A loading device for loading an IUD into a distal end of an IUD insertion device during a manufacturing process wherein the IUD insertion device comprises an elongated sheath, and a plunger disposable within a lumen of the elongated sheath, a handle, and an IUD insertion device slider positioned on the handle of the IUD insertion device, the IUD comprises a t-shaped body with an elongated body and a flexible member secured to an end of the elongated body, wherein the loading device comprises:

an elongated planar base having a first planar base end, a second planar base end, an upper surface and a lower surface configured to engage the IUD insertion device on the upper surface of the elongated planar base of the loading device;

an IUD retainer positioned on the upper surface of the elongated planar base of the loading device towards the first planar base end;

a loading device clamp having a first clamp end on a first side and a second clamp end on a second side opposite the first side, wherein the loading device clamps is positioned on the upper surface of the elongated planar base of the loading device towards the first planar base end having an open configuration and a closed configuration and a linear aperture therethrough and the first clamp end positionable to engage the elongated sheath of the IUD insertion device wherein the linear aperture of the loading device at the loading device first clamp end has a first clamp end aperture diameter which tapers to a central aperture diameter and a second clamp end diameter at the loading device second clamp end which tapers to the central aperture diameter; and pneumatic controls configured to draw the flexible member of the IUD through the aperture of the loading device clamp and into the lumen of the IUD insertion device, wherein the IUD retainer is positioned adjacent the second clamp end and further wherein the IUD retainer holds the IUD adjacent the loading device clamp prior to loading the IUD into the distal end of the IUD insertion device during the manufacturing process.

8. The loading device of claim 7 wherein the loading device clamp is openable about a hinge.

9. The loading device of claim 7 wherein a IUD insertion device retainer is a hypotube.

10. The loading device of claim 7 wherein the IUD retainer comprises a channel for one or more flexible members of the IUD.

11. The loading device of claim 7 further comprising a vacuum applicator.

12. A method of inserting an IUD into an IUD insertion device during a manufacturing process wherein the IUD insertion device comprises an elongated sheath, and a plunger disposable within a lumen of the elongated sheath, a handle, and an IUD insertion device slider positioned on the handle wherein the method of using an IUD loading device comprises:

providing an IUD loading device wherein the IUD loading device comprises:

an elongated planar base having a first planar base end, a second planar base end, an upper surface and a lower surface configured to engage the IUD insertion device on the upper surface of the elongated planar base of the IUD loading device, a linear loading device slider positioned on the upper surface of the elongated planar base, a support plate secured to a portion of the linear loading device slider, a hinged loading device clamp positioned on the upper surface of the elongated planar base of the IUD loading device towards the first planar base end having an open configuration and a closed configuration having a first clamp end positionable to engage the elongated sheath of the IUD insertion device and a linear aperture therethrough wherein the linear aperture of the hinged loading device clamp at the first clamp end has a first clamp end aperture diameter which tapers to a central aperture diameter and a second clamp end diameter at a second clamp end which tapers to the central aperture diameter, an IUD insertion device retainer, and an IUD retainer positioned on the upper surface of the elongated planar base of the IUD loading device towards the second planar base end wherein the IUD insertion device retainer is configured to be inserted within a portion of the handle of the IUD insertion device to secure the IUD insertion device to the loading device IUD;

positioning the IUD in the IUD retainer of the IUD loading device;

placing the IUD insertion device in the IUD insertion device retainer of the IUD loading device;

positioning a distal end of the IUD insertion device adjacent a second aperture in the hinged loading device clamp; and applying a vacuum on the IUD insertion device retainer and drawing one or more flexible members of the IUD into an aperture in the IUD insertion device.

13. The method of inserting the IUD into the IUD insertion device of claim 12 further comprising passing a hypotube through a proximal end of the IUD insertion device.

14. The method of inserting the IUD into the IUD insertion device of claim 12 further comprising feeding flexible members of the IUD into a —first aperture of the hinged loading device clamp.

15. A loading device for loading an IUD into an IUD insertion device during a manufacturing process wherein the IUD insertion device comprises an elongated sheath, and a plunger disposable within a lumen of the elongated sheath, a handle, and an IUD insertion device slider positioned on the handle of the IUD insertion device wherein the loading device means comprises:
- an elongated planar base having a first planar base end, a second planar base end, an upper surface and a lower surface configured to engage the IUD insertion device on the upper surface of the elongated planar base of the loading device means;
- a linear loading device slider means positioned on the upper surface of the elongated planar base;
- a support plate secured to a portion of the linear loading device slider;
- a hinged loading device clamp means positioned on the upper surface of the elongated planar base of the loading device means towards the first planar base end having a linear aperture therethrough and having a first clamp end positionable to engage the elongated sheath of the IUD insertion device and a second clamp end, wherein the linear aperture of the hinged loading device clamp means has a first clamp end aperture diameter which tapers to a central aperture diameter and a second clamp end aperture diameter which tapers to the central aperture diameter;
- an IUD insertion device retainer means configured to retain the handle of the IUD insertion device; and
- an IUD retainer means positioned adjacent the second clamp end wherein the IUD retainer means holds the IUD prior to loading the IUD into a distal end of the IUD insertion device during the manufacturing process.

16. The loading device means of claim 15 further comprising a pneumatic control.

17. The loading device means of claim 15 further comprising a vacuum applicator.

18. The loading device means of claim 15 wherein the hinged loading device clamp means is openable about a hinge.

19. The loading device means of claim 15 wherein the IUD insertion device retainer means is a hypotube.

20. The loading device means of claim 15 wherein the IUD retainer means comprises a channel for one or more flexible members of the IUD.

\* \* \* \* \*